United States Patent
Kim et al.

(10) Patent No.: US 11,219,653 B2
(45) Date of Patent: Jan. 11, 2022

(54) COMPOSITION FOR ENHANCING IMMUNITY, CONTAINING GINSENG BERRY POLYSACCHARIDES

(71) Applicants: AMOREPACIFIC CORPORATION, Seoul (KR); KYONGGI UNIVERSITY INDUSTRY & ACADEMIA COOPERATION FOUNDATION, Suwon-si (KR)

(72) Inventors: Suhwan Kim, Yongin-si (KR); Juewon Kim, Yongin-si (KR); Chan-woong Park, Yongin-si (KR); Dae Bang Seo, Yongin-si (KR); Donghyun Cho, Yongin-si (KR); Kwang Soon Shin, Yongin-si (KR); Dae Young Lee, Yongin-si (KR)

(73) Assignees: AMOREPACIFIC CORPORATION, Seoul (KR); KYONGGI UNIVERSITY INDUSTRY & ACADEMIA COOPERATION FOUNDATION 1, Gyeonggi-do (KR)

( * ) Notice: Subject to any disclaimer, the term of this patent is extended or adjusted under 35 U.S.C. 154(b) by 188 days.

(21) Appl. No.: 16/481,295

(22) PCT Filed: Jan. 26, 2018

(86) PCT No.: PCT/KR2018/001185
§ 371 (c)(1),
(2) Date: Jul. 26, 2019

(87) PCT Pub. No.: WO2018/139898
PCT Pub. Date: Aug. 2, 2018

(65) Prior Publication Data
US 2021/0128660 A1 May 6, 2021

(30) Foreign Application Priority Data
Jan. 26, 2017 (KR) .......................... 10-2017-0013005

(51) Int. Cl.
*A61K 36/258* (2006.01)
*A61K 31/715* (2006.01)

(52) U.S. Cl.
CPC .......... *A61K 36/258* (2013.01); *A61K 31/715* (2013.01)

(58) Field of Classification Search
None
See application file for complete search history.

(56) References Cited

U.S. PATENT DOCUMENTS 10,086,028 B2 * 10/2018 Park .................. A61Q 19/02
2017/0189464 A1    7/2017 Lee et al.

FOREIGN PATENT DOCUMENTS

| CN | 101157731 A | 4/2008 |
|---|---|---|
| CN | 101810323 A | 8/2010 |
| KR | 1020090032501 A | 4/2009 |
| KR | 2009 045134 * | 5/2009 |
| KR | 1020130100089 A | 9/2013 |
| KR | 101487542 B1 | 1/2015 |

OTHER PUBLICATIONS

Wang, Y. et al. Extraction, Characterization of a Ginseng Fruits Polysaccharide and its Immune Modulating Activities in Rats with Lewis Lung Carcinoma. Carbohydrate Polymers 127:215-221, 2015. (Year: 2015).*
Ross, K. et al. Characterization of Water Extractable Crude Polysaccharides from Cherry, Raspberry, and Ginseng Berry Fruits. Int J of Food Properties 18(3)670-689, 2015. (Year: 2015).*
Byeon, S. et al. Molecular Mechanism of Macrophage Activation by Red Ginseng Acidic Polysaccharide from Korean Red Ginseng. Mediators of Inflammation 1-7, 2012. (Year: 2012).*
Kwak, Y. et al. Anti-Hypertensive Effects of Red Ginseng Acidic Polysaccharide from Korean Red Ginseng. Biological & Pharmaceutical Bulletin 33(3)468-472, 2010. (Year: 2010).*
Extended European Search Report dated Sep. 2, 2020, issued in EP 187454418.8, 11 pages.
Jin-Yi Wan et al., "Multiple Effects of Ginseng Berry Polysaccharides: Plasma Cholesterol Level Reduction and Enteric Neoplasm Prevention," The American Journal of Chinese Medicine, 2017, vol. 45, No. 6, pp. 1293-1307.
Wei Zhang et al., "Ginseng Berry Extract Promotes Maturation of Mouse Dendritic Cells," Plos One, 2015, vol. 10, No. 6, e0130926.
Extended European Search Report dated Sep. 2, 2020, issued in EP 18745441.8, 11 pages.
International Search Report for International Application No. PCT/KR2018/001185, International Filing Date Jan. 26, 2018, dated May 8, 2018, 4 pages.
Yingyu Wang et al., "Extraction, characterization of a Ginseng fruits polysaccharide and its immune modulating activities in rats with Lewis lung carcinoma", Carbohydrate Polymers, 2015, vol. 127, pp. 215-221.
English Translation of Office Action dated Apr. 27, 2021 issued in Chinese patent application No. 201880015262.1.
Feng Mengxin, "Fractionation, Purification, Physicochemical Properties and Antitumor Activity of Polysaccharides from Panax ginseng Fruit", Chinese Excellent Master's Degree Thesis Full-text Database Medical and Health Science Technology Series, 2016, No. 8, E057-123.

(Continued)

*Primary Examiner* — Ralph J Gitomer
(74) *Attorney, Agent, or Firm* — Cantor Colburn LLP

(57) ABSTRACT

The specification relates to a composition for enhancing immunity, comprising a ginseng berry polysaccharide as an active ingredient. The composition can increase the expression of cytokines such as IL-6, IL-12, and TNF-α by using ingredients derived from natural products. In addition, the composition can exhibit excellent immunity enhancement effects because of the unique components and structure of a ginseng berry polysaccharide.

6 Claims, 8 Drawing Sheets

(56) References Cited

OTHER PUBLICATIONS

Kelly Ross et al., "Characterization of Water Extractable Crude Polysaccharides from Cherry, Raspberry, and Ginseng Berry Fruits: Chemical Composition and Bioactivity", International Journal of Food Properties, 2015, No. 18, pp. 670-689.
Liu Chunlan, "Isolation Purification and Characterization of Panax Ginseng Fruit Polysaccharide", China Academic Journal Electronic Publishing House, 1995, vol. 2, pp. 142-147, with English Abstract.
Office Action dated Apr. 27, 2021 issued in Chinese patent application No. 201880015262.1.

* cited by examiner

COMPOSITION FOR ENHANCING IMMUNITY, CONTAINING GINSENG BERRY POLYSACCHARIDES

This application is a national stage application of PCT/KR2018/001185, filed Jan. 26, 2018, which claims priority to KR 10-2017-0013005 filed Jan. 26, 2017, both/all of which are hereby incorporated by reference in their entirety.

TECHNICAL FIELD

The present specification describes a composition for enhancing immunity, comprising a ginseng berry polysaccharide.

BACKGROUND ART

It is likely to become vulnerable to various infections or diseases when the body's immune function deteriorates. Macrophage is a cell which regulates the immune phenomenon by secreting various cytokines in the course of phagocytosis and elimination of bacteria or foreign substances and plays a pivotal role in the immune response to the antigen. Macrophages are involved in antigen presentation and non-specific immune responses of lymphocytes and exhibit direct tumor cell-damaging activity. In addition, TLR (tool like receptor)-responding substances (LPS or natural products) are known to activate macrophages and produce cytokines such as IL-1, IL-6, IL-10, IL-12, and TNF-$\alpha$, which can regulate proliferation of T cells and B cells, phagocytosis, and secondary immune responses such as protection against microbial infection.

IL-1, IL-6, and TNF-$\alpha$ are representative cytokines induced by macrophages and are known to play a pivotal role in the inflammatory response as a result of bacterial infection and be increased in inflammatory lesions. It has been reported that IL-6 cooperatively acts with IL-1 to be involved in the differentiation of T cells and B cells. TNF-$\alpha$ is known to have an antiviral action and play an important role in various biological reactions. In addition, IL-12 is a cytokine which induces NK cell activation and Th1-type immune response and is known to enhance the responsiveness to cellular foreign substances.

There is a demand for ingredients which are derived from natural products and effective in such immunity enhancement.

SUMMARY OF INVENTION

Technical Problem

In an aspect, a problem to be solved by the present invention is to provide a composition exhibiting an excellent immunity enhancement effect.

In another aspect, a problem to be solved by the present invention is to provide a composition for increasing the expression of IL-6, IL-12, and TNF-$\alpha$.

In still another aspect, a problem to be solved by the present invention is to provide a composition comprising an ingredient which is derived from a natural product and exhibits an excellent immunity enhancement effect.

In yet another aspect, a problem to be solved by the present invention is to provide a composition which is an ingredient derived from a natural product and exhibits little or no toxicity or side effects.

In yet still another aspect, a problem to be solved by the present invention is to provide a composition capable of playing a health supporting role as a result of immunity enhancement.

Solution to Problem

In an aspect, the present invention provides a composition for enhancing immunity, comprising a ginseng berry polysaccharide as an active ingredient.

Advantageous Effects of Invention

In an aspect, the present invention can provide a composition exhibiting an excellent immunity enhancement effect.

In another aspect, the present invention can provide a composition which increases the expression of IL-6, IL-12, and TNF-$\alpha$.

In still another aspect, the present invention can provide a composition comprising an ingredient which is derived from a natural product and exhibits an excellent immunity enhancement effect.

In yet another aspect, the present invention can provide a composition capable of playing a health supporting role as a result of immunity enhancement.

DESCRIPTION OF EMBODIMENTS

Figure 1:
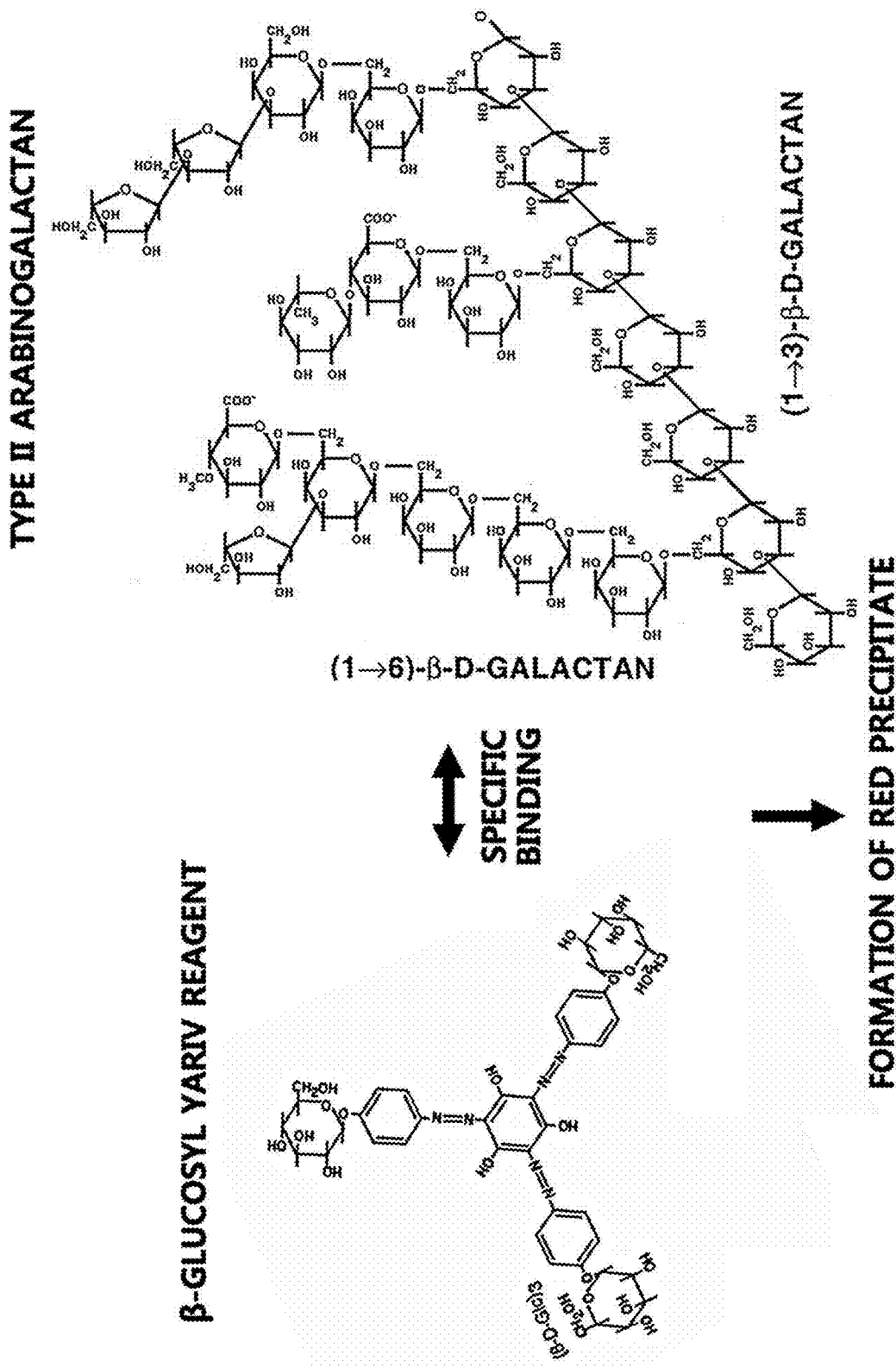
FIG. 1 schematically illustrates a reaction for detecting arabinogalactan using $\beta$-glucosyl Yariv reagent.

Hereinafter, embodiments of the present application will be described in more detail with reference to the accompanying drawings. However, the techniques disclosed in the present application are not limited to the embodiments described herein but may be embodied in other forms. It should be understood, however, that the embodiments disclosed herein are provided so that this disclosure will be thorough and complete and will fully convey the scope of the present application to those skilled in the art. In the drawings, the widths and thicknesses of constituents are slightly enlarged in order to clearly illustrate each constituent. In addition, although only a part of the constituents is illustrated for convenience of explanation, those skilled in the art can easily grasp the rest of the constituents. It will be apparent to those skilled in the art that various modifications and variations can be made in the present application without departing from the spirit and scope of the present application.

According to an embodiment of the present invention, there can be provided a composition for enhancing immunity, comprising a ginseng berry polysaccharide as an active ingredient. The ginseng berry polysaccharide exhibits an effect of modulating the immune function by the unique components and structure thereof, and specifically, the ginseng berry polysaccharide exhibits an excellent effect of activating cytokines. Consequently, the composition according to the embodiments of the present invention can exhibit a remarkably excellent immunity enhancement effect.

The ginseng berry polysaccharide may be a polysaccharide component derived from the berry part in the aboveground part of ginseng (*Panax* ginseng C. A. Meyer). In an example, the ginseng berry may be a part comprising fruit pulp, fruit skin, or both the fruit pulp and fruit skin of ginseng.

The ginseng berry polysaccharide can be obtained from extracted insoluble components which are not dissolved in ethanol after subjecting ginseng berries to extraction using ethanol. For example, it is possible to separate only a water-soluble component by subjecting the extracted ethanol-insoluble components to extraction using water and to use a ginseng berry polysaccharide comprised in this water-soluble component as an active ingredient. For example, a ginseng berry polysaccharide can be obtained by concentrating the water-soluble component, precipitating the concentrated water-soluble component using ethanol, and then removing low molecular weight components.

For example, a water-soluble extract can be obtained by subjecting ginseng berries from which seeds have been removed to extraction using 50% to 100% ethanol and then subjecting the extracted insoluble components to thermal extraction using water in a volume to be 3 to 10 times the volume of the extracted insoluble components. The water-soluble extract is concentrated so as to have a solid content of 10 to 50 wt %, precipitated using ethanol in a volume to be 2 to 5 times the volume of the water-soluble extract, and separated to have a molecular weight cut off of 10,000 to 30,000 and thus to remove the low molecular weight components. The removal of the low-molecular weight components may be performed by filtration such as ultrafiltration using an ultrafiltration membrane, dialysis, and a dissolution treatment repeated 1 to 10 times using 50% to 100% ethanol in a 2 to 10-fold volume. In an example, drying may be performed after removal of the low molecular weight components. The drying may be performed by freezing, hot air, spraying, or vacuum treatment.

In an example, an enzyme treatment may be further comprised before subjecting the water-soluble components of ginseng berry to extraction using water. As the enzyme, any enzyme can be used without restriction as long as it is an enzyme used in food. The enzyme may be selected from, for example, amylase, protease, pectinase, lipase, cellulase, xylanase, β-glucanase, or pullulanase. The immunity activity of the composition can be increased by the enzyme treatment. The enzyme treatment can be performed by, for example, reacting the water-soluble components with an enzyme at 40° C. to 60° C. for 10 to 60 minutes.

The ginseng berry polysaccharide may comprise arabinose, galactose, galacturonic acid, and glucuronic acid.

In an example, galacturonic acid and glucuronic acid may be comprised in the composition at a total content of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, 7 wt % or more, 8 wt % or more, 9 wt % or more, or 10 wt % or more and 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, or 4 wt % or less with respect to the total weight of the polysaccharide. For example, the content may be from 0.1 wt % to 25 wt % or from 0.5 wt % to 20 wt %.

The galacturonic acid may be comprised in the composition at a content of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, 7 wt % or more, 8 wt % or more, 9 wt % or more, or 10 wt % or more and 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, or 4 wt % or less with respect to the total weight of the polysaccharide. The content may be, for example, from 0.1 wt % to 20 wt %, from 0.1 wt % to 15 wt %, from 1 wt % to 5 wt %, from 5 wt % to 15 wt %, or from 0.5 wt % to 5 wt %.

The glucuronic acid may be comprised in the composition at a content of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, or 7 wt % or more and 10 wt % or less, 9 wt % or less, 8 wt % or less, 7 wt % or less, 6 wt % or less, 5 wt % or less, or 4 wt % or less with respect to the total weight of the polysaccharide. The content may be, for example, from 0.1 wt % to 10 wt %, from 0.5 wt % to 5 wt %, or from 0.1 wt % to 5 wt %.

In an example, the arabinose may be comprised in the composition at a content of from 2 wt % to 30 wt % with respect to the total weight of the polysaccharide.

In an example, the galactose may be comprised in the composition at a content of from 5 wt % to 50 wt % with respect to the total weight of the polysaccharide.

The ginseng berry polysaccharide comprises an arabinogalactan structure at a high proportion and can thus exhibit excellent immunity activity. The arabinogalactan structure can be detected using (3-glucosyl Yariv reagent. The β-glucosyl Yariv reagent is (1,3,5-tri-(4-β-glucopyranosyl-oxyphenylazo)-2,4,6-trihydroxybenzene) and specifically reacts with type II arabino-β-3,6-galactan among arabinogalactans to form a red precipitate. The concentration of the arabinogalactan structure is proportional in a concentration dependent manner to the area of the red precipitate ring generated by the treatment using β-glucosyl Yariv reagent. The ginseng berry polysaccharide can have a precipitate ring area having a size of 40% or more, 50% or more, 60% or more, 70% or more, or 80% or more and 90% or less, 80% or less, 70% or less, or 60% or less when the size of precipitate generated in the standard arabino-β-3,6-galactan at the same concentration is 100%. The precipitate area may be, for example, from 50% to 90% or from 50% to 80%.

The weight average molecular weight of the ginseng berry polysaccharide may be 10 kDa or more. The ginseng berry polysaccharide may have a main peak at a molecular weight of from 70 kDa to 80 kDa. The ginseng berry polysaccharide exhibits a remarkably excellent effect of activating cytokines related to the immune function. For example, the ginseng berry polysaccharide can exhibit an excellent immunity enhancement effect by increasing the expression of IL-6, IL-12, and TNF-α in macrophages.

The composition according to the embodiments of the present invention may be provided as various forms of food additives or functional foods comprising the active ingredient. The composition may be processed into fermented milk, cheese, yogurt, juice, probiotic preparations, and health foods comprising the active ingredient and may be used in the form of various other food additives.

The composition according to the embodiments of the present invention may be a composition for health food.

The composition for health food according to an embodiment of the present invention may comprise the active ingredient at, but not limited to, from 0.0001 wt % to 99 wt %, for example, from 0.01 wt % to 60 wt % with respect to the total weight of the composition.

In a specific example, the composition for health food may be formulated into a pill, a capsule, a tablet, a granule, a caramel, or a drink. In another embodiment, the composition may be processed in the form of a liquid, a powder, a granule, a tablet, or a tea bag.

The composition may be administered by various methods such as simple drinking, injection administration, spraying, or squeezing.

The composition may comprise other components and the like that can add a synergistic effect to the main effect within a range in which the main effect of the present invention is not impaired. For example, the composition may further comprise additives such as a perfume, a coloring agent, a bactericide, an antioxidant, an antiseptic, a moisturizing agent, a thickener, an inorganic salt, an emulsifier, and a synthetic polymer material to improve physical properties. In addition, the composition may further comprise auxiliary components such as water-soluble vitamins, oil-soluble vitamins, high molecular weight peptides, high molecular weight polysaccharides, and seaweed extracts. The above components may be appropriately chosen and mixed by those skilled in the art depending on the formulation or use purpose, and the added amount thereof can be selected within a range in which the objects and effects of the present invention are not impaired. For example, the amount of the above components added may be, but not limited to, from 0.01 wt % to 5 wt %, for example, from 0.01 wt % to 3 wt % based on the total weight of the composition.

In an embodiment, the composition may be a cosmetic composition.

The cosmetic composition according to an embodiment of the present invention may comprise the active ingredient at, but is not limited to, from 0.0001 wt % to 99 wt %, for example, from 0.01 wt % to 60 wt % based on the total weight of the composition.

The cosmetic composition according to an embodiment of the present invention may be formulated comprising a cosmetically or dermatologically acceptable medium or base. The cosmetic composition may be provided in the form of a suspension, a microemulsion, a microcapsule, a microgranule, or ionic (liposome) and non-ionic vesicular dispersions or in the form of a cream, a skin lotion, a lotion, a powder, an ointment, a spray, or a stick concealer as all formulations suitable for topical application. The cosmetic composition may also be used in the form of a foam or in the form of an aerosol composition further comprising a compressed propellant. These compositions may be prepared according to conventional methods in the art.

In addition, the cosmetic composition according to the embodiments of the present invention may comprise adjuvants commonly used in the field of cosmetics or dermatology, such as a powder, a fat substance, an organic solvent, a solubilizing agent, a thickening agent, a gelling agent, a softening agent, an antioxidant, a suspending agent, a stabilizer, a foaming agent, a surfactant, water, an ionic or nonionic emulsifier, a filler, a sequestering agent, a chelating agent, a preservative, a vitamin, a blocking agent, a wetting agent, an essential oil, a dye, a pigment, a hydrophilic or lipophilic active agent, a lipid vesicle, or any other ingredients commonly used in cosmetics. The adjuvants are introduced in amounts commonly used in the field of cosmetics or dermatology. The cosmetic composition according to the embodiments of the present invention may further comprise a skin absorption promoting substance to increase the skin improving effect.

In an embodiment of the present invention, the composition may be a pharmaceutical composition.

The pharmaceutical composition according to the present specification may be various oral or parenteral formulations. In the case of being formulated into a preparation, the preparation is prepared using a diluent or excipient such as a filler, an extender, a binder, a wetting agent, a disintegrating agent, or a surfactant. A solid preparation for oral administration comprises a tablet, a pill, a powder remedy, a granule, a soft or hard capsule, and the like. Such a solid preparation is prepared by mixing one or more compounds with at least one or more excipients, for example, starch, calcium carbonate, sucrose or lactose, or gelatin. In addition to simple excipients, lubricants such as magnesium stearate and talc are also used. A liquid preparation for oral administration comprises a suspension, an internal solution, an emulsion, and a syrup. The liquid preparation may comprise various excipients, for example, a wetting agent, a sweetener, a fragrance, and a preservative in addition to commonly used simple diluents such as water and liquid paraffin. A preparation for parenteral administration comprises a sterilized aqueous solution, a non-aqueous solution, a suspension, an emulsion, a freeze-dried preparation, and a suppository. Propylene glycol, polyethylene glycol, vegetable oils such as olive oil, an injectable ester such as ethyl oleate, and the like may be used as the non-aqueous solvent and solvent for suspension. Witepsol, macrogol, tween 61, cacao butter, laurin oil and fat, glycerogelatin and the like may be used as the base for suppository.

As the pharmaceutical dose form of the composition of the present specification, the composition may also be used in the form of a pharmaceutically acceptable salt of these and the composition may also be used singly or in combination with other pharmaceutically active compounds as well as in suitable aggregation. The salt is not particularly limited as long as it is pharmaceutically acceptable, and for example, hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methanesulfonic acid, benzenesulfonic acid, toluenesulfonic acid, and naphthalenesulfonic acid can be used.

The composition of the present specification may be parenterally or orally administered depending on the purpose. The composition may be administered from one time to several divided times so as to be administered in an amount of 0.1 to 500 mg, preferably 1 to 100 mg per kg of the body weight per day. The dosage for a particular patient may vary depending on the patient's body weight, age, gender, health condition, diet, administration time, administration method, excretion rate, severity of disease, and the like.

The pharmaceutical composition according to the present specification can be used by being formulated in any form suitable for pharmaceutical preparations, comprising oral formulations such as a powder remedy, a granule, a tablet, a soft or hard capsule, a suspension, an emulsion, a syrup, and an aerosol, external preparations for skin such as an ointment and a cream, a suppository, an injection, a sterilized injection solution, and the like, according to conventional methods, respectively.

According to another embodiment of the present invention, there can be provided a method for enhancing immunity which comprises administering a ginseng berry polysaccharide to a subject in need of immunity enhancement. The ginseng berry polysaccharide is the same as that described in the composition for enhancing immunity according to an embodiment of the present invention described above, and thus the description thereon is omitted.

According to still another embodiment of the present invention, there can be provided use of a ginseng berry polysaccharide for preparation of a composition for enhancing immunity. The ginseng berry polysaccharide and composition for enhancing immunity are the same as those described in the composition for enhancing immunity according to an embodiment of the present invention described above, and thus the description thereon is omitted.

EMBODIMENTS

Hereinafter, the present invention will be described in more detail with reference to Examples. It is to be understood by those skilled in the art that these Examples are merely illustrative of the present invention and that the scope of the present invention is not construed as being limited by these Examples.

[Preparation Example 1] Preparation of Ginseng Berry Polysaccharide

Figure 2:
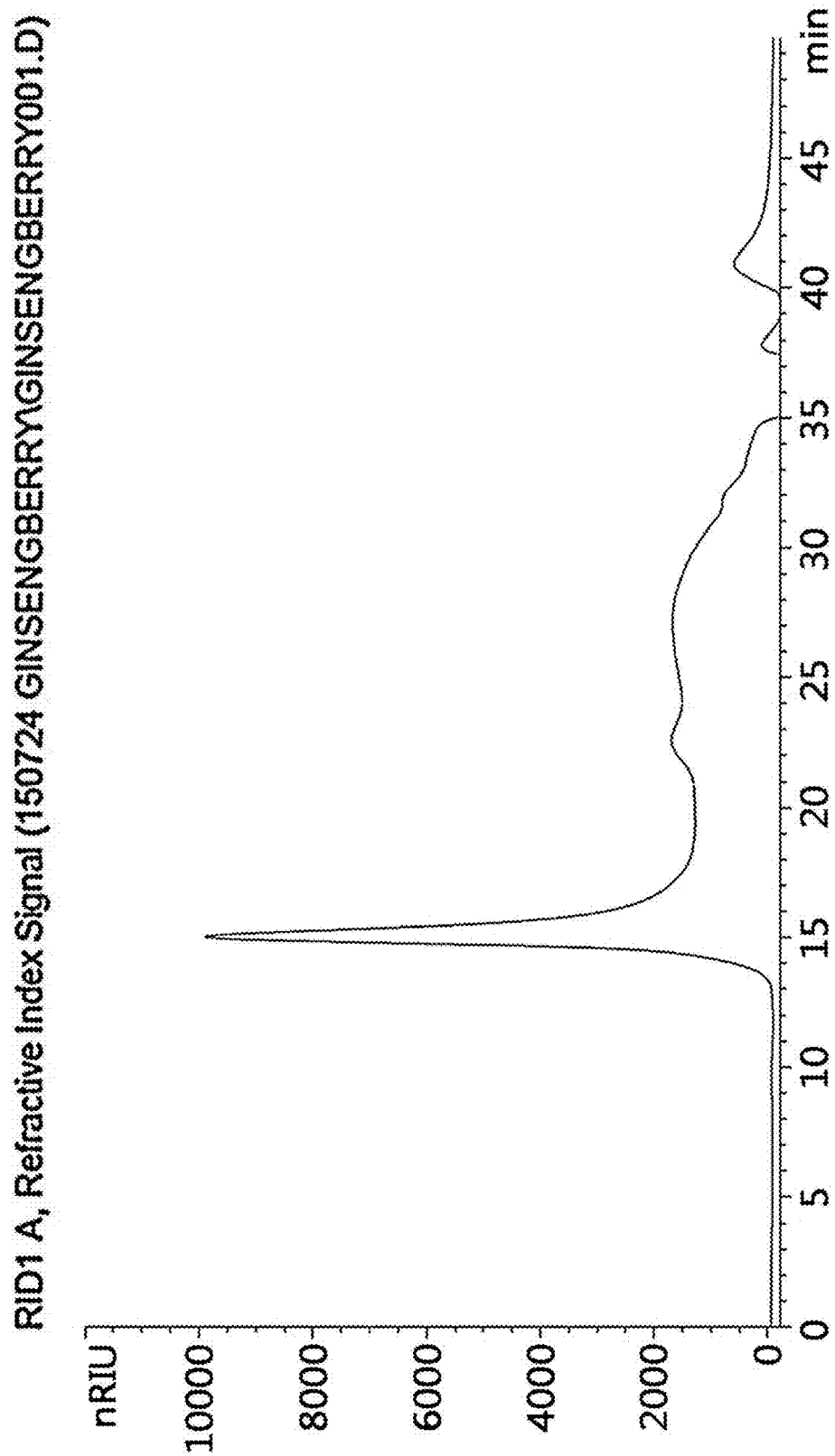
FIG. 2 is a graph which illustrates a fraction of a water-soluble substance in a ginseng berry.
Figure 3:
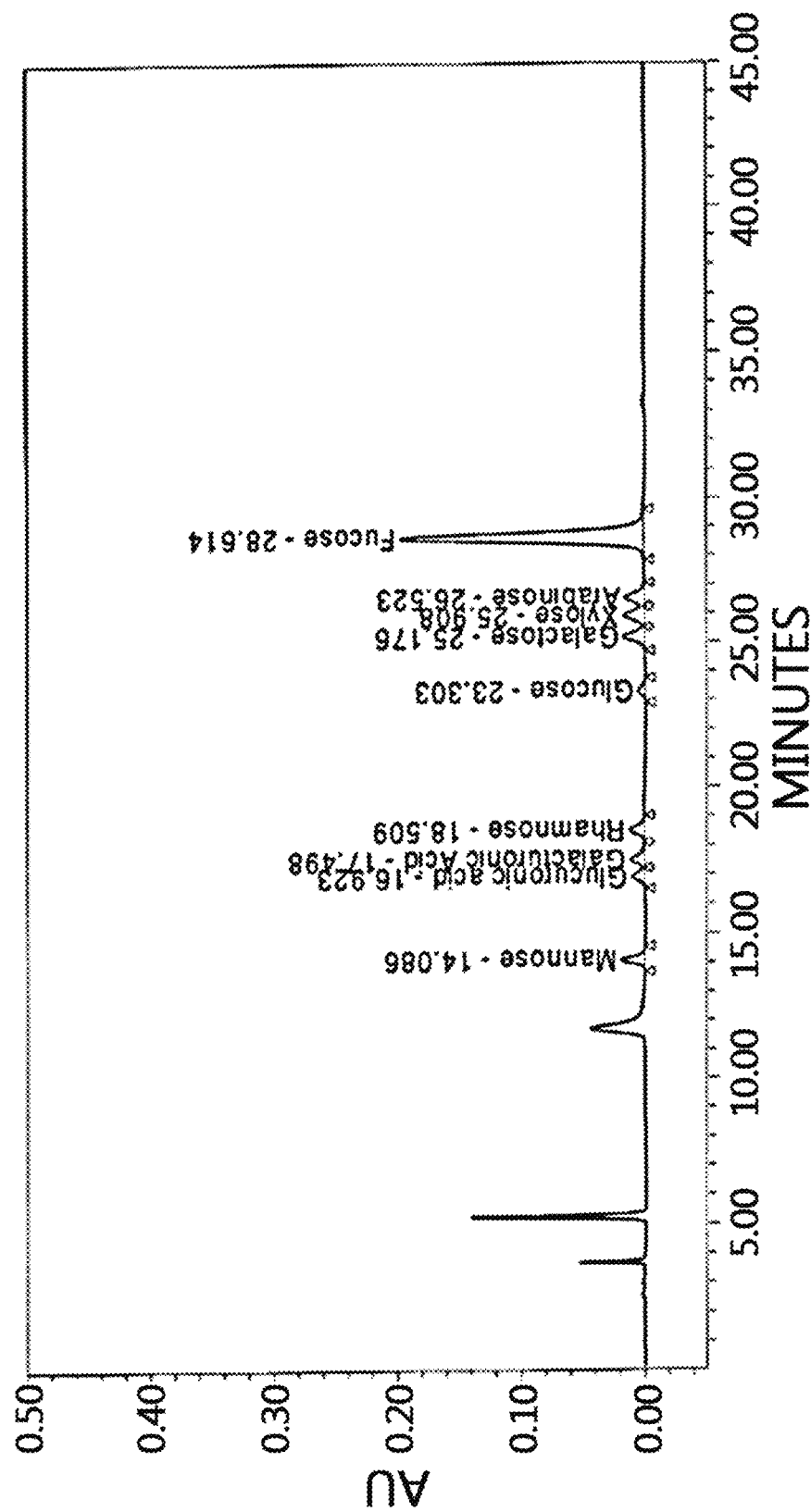
FIG. 3 is a graph which illustrates the chromatographic results for a ginseng berry polysaccharide.

Ginseng berries from which seeds had been removed were subjected to extraction using 90% ethanol in a volume to be 10 times the volume of the ginseng berries, the water-soluble components were precipitated, and the supernatant was removed. The extracted and precipitated insoluble components were subjected to thermal extraction at a temperature of 90° C. for 5 hours using water in a volume to be 20 times the volume of the water-soluble components. The extract was concentrated so as to have a solid content of 30 wt %, 90% ethanol in a volume to be 2 times the volume of the concentrate was added to the concentrate, and the concentrate was precipitated. The results of high performance liquid chromatography (HPLC) for the precipitated water-soluble components are illustrated in FIG. 2. The precipitate was separated by ultrafiltration to have a molecular weight cut off of 20,000 and thus to remove low molecular weight components, and the separated precipitate was freeze-dried to obtain a ginseng berry polysaccharide having a molecular weight of 10 kDa or more and a main peak at a molecular weight of from 70 to 80 kDa. The results of high performance liquid chromatography (HPLC) for the ginseng berry polysaccharide thus prepared are illustrated in FIG. 3.

[Preparation Example 2] Preparation of Red Ginseng Polysaccharide

A red ginseng polysaccharide was prepared in the same manner as in Preparation Example 1 except that red ginseng root was used instead of ginseng berries.

[Test Example 1] Detection of Arabinogalactan

The reactivity with β-glucosyl Yariv reagent (Biosupplies, Parkville, Australia) to confirm the presence of arabinose-β-3,6-galactan was measured by single radical gel diffusion according to the method of Holst and Clarke (Van Holst G J, Clarke A E. Quantification of arabinogalactan-protein in plant extracts by single radial gel diffusion. Anal. Chem. 148: 446-450 (1985)).

Figure 4:
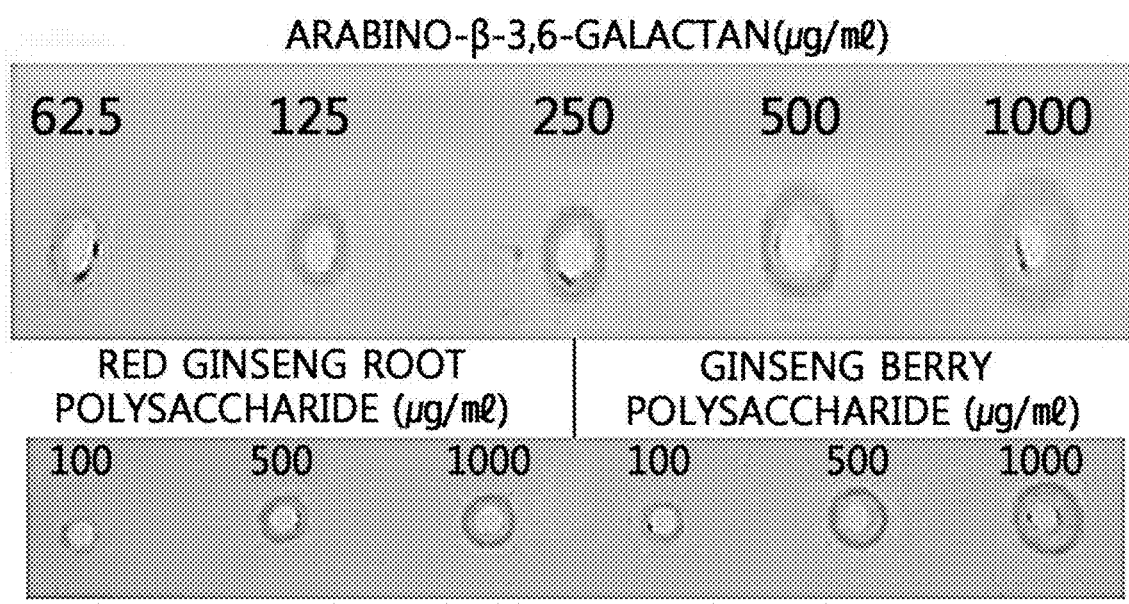
FIG. 4 is a photograph which illustrates precipitate rings of a standard substance, a ginseng berry polysaccharide, and a red ginseng root polysaccharide generated by a treatment using $\beta$-glucosyl Yariv reagent.

A 0.15 M NaCl agarose plate comprising β-glucosyl Yariv reagent at 10 μg/ml was fabricated, a well having a diameter of 2.5 mm was fabricated, and a solution comprising gum Arabic, which was a standard substance diluted to have various concentrations, and sample at 5 μg was injected into each well. The plate was allowed to still stand for 15 hours in a wet state for reaction, the presence or absence of arabinose-β-3,6-galactan was observed by observing the red precipitate thus generated, and the reactivities between the samples and the β-glucosyl Yariv reagent were compared with each other by calculating the areas of the precipitate rings generated. As the samples, the standard substance was used at concentrations of 62.5, 125, 250, 500, and 1000 μg/ml and the polysaccharides prepared in Preparation Example 1 and Preparation Example 2 were used at concentrations of 100, 500 and 1000 μg/ml, respectively, as illustrated in FIG. 4.

Figure 5:
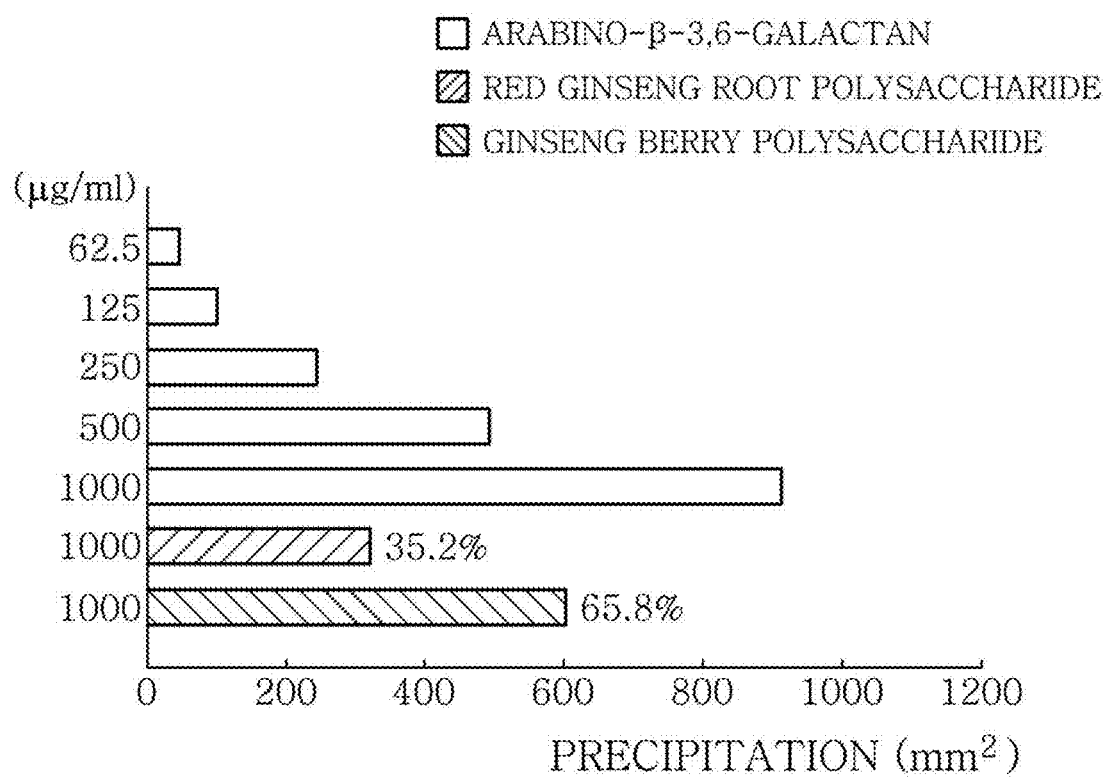
FIG. 5 is a graph which illustrates the areas of precipitate rings of a standard substance, a ginseng berry polysaccharide, and a red ginseng root polysaccharide generated by a treatment using $\beta$-glucosyl Yariv reagent.

The area of the red precipitate ring generated was measured, and the relative content of arabino-β-3,6-galactan is illustrated in FIG. 5. The results in FIG. 5 are obtained by comparing the areas of the groups treated with the respective samples at a concentration of 1000 μg/ml with respect to the group treated with the standard substance at a concentration of 1000 μg/ml.

From the results illustrated in FIG. 5, it can be confirmed that the ginseng berry polysaccharide comprises an arabinogalactan structure at a high content to be 2 times or more that in the red ginseng polysaccharide.

[Test Example 2] Evaluation on IL-6 Production Ability in Macrophage

The IL-6 production ability of ginseng berry polysaccharide in macrophages was measured as follows.

BALB/c mice were intraperitoneally injected with 1 ml of 5% thioglycollate, after 3 days, the mice were sacrificed by cervical dislocation, and peritoneal exudative cells (PEC) were collected by intraperitoneal injection of 10 mL of DMEM medium. The collected PECs were dispensed into a 96-well culture plate so as to have a concentration of $2.0 \times 10^5$ cells/well, cultured for 2 hours to attach macrophages to the plate, and then washed with the culture medium to remove unattached cells. The sample was added to the macrophages so that the final concentration of the sample solution of ginseng berry-purified fraction was 0.8 μg/ml to 100 μg/ml, and the cells were cultured for 72 hours. After completion of the culturing, centrifugation was performed at 900 rpm for 5 minutes to collect 150 μl of supernatant of the cell culture medium, and the content of IL-6, an inducible secretory cytokine, in the culture supernatant was measured. The results are illustrated in FIG. 6.

The polysaccharides of Preparation Example 1 and Preparation Example 2 were used as the samples and PSK (Krestin™, from *Coriolus versicolor*), CVT200 (COLD-FX) prepared from *Panax quinquefolius* root, and Biobran (arabinoxylan compound) were used as the positive controls. In FIG. 6, NC denotes a non-treated group and PC denotes a group treated with LPS at 5 μg/ml.

Figure 6:
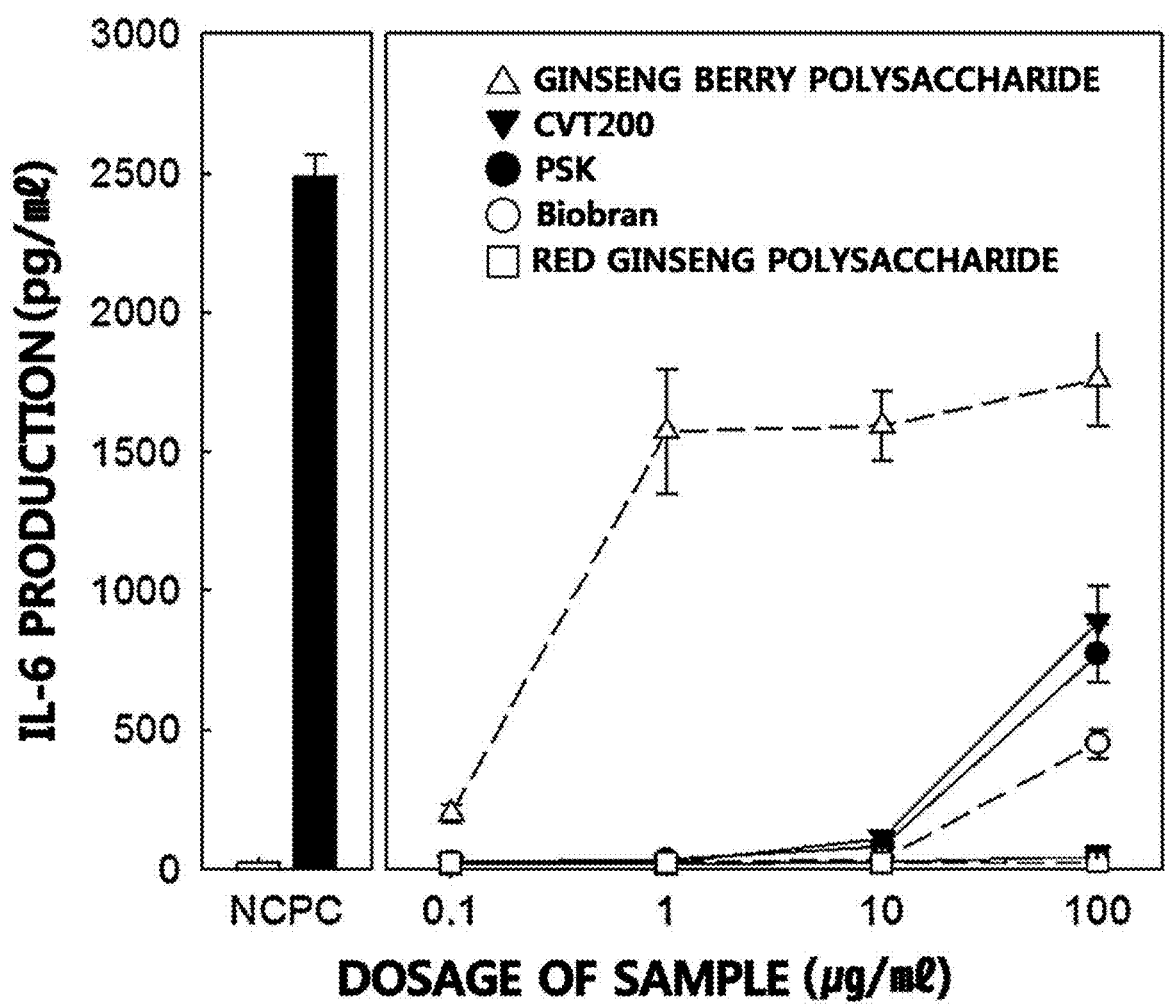
FIG. 6 is a graph which illustrates the IL-6 production ability of a sample in macrophages.

From the results illustrated in FIG. 6, it can be seen that the ginseng berry polysaccharide exhibits remarkably excellent IL-6 production ability as compared with the samples used as the positive control and the red ginseng polysaccharide.

[Test Example 3] Evaluation on IL-12 Production Ability in Macrophage

The IL-12 production ability of ginseng berry polysaccharide in macrophages was measured as follows.

BALB/c mice were intraperitoneally injected with 1 ml of 5% thioglycollate, after 3 days, the mice were sacrificed by cervical dislocation, and peritoneal exudative cells (PEC) were collected by intraperitoneal injection of 10 mL of DMEM medium. The collected PECs were dispensed into a 96-well culture plate so as to have a concentration of $2.0 \times 10^5$ cells/well, cultured for 2 hours to attach macrophages to the plate, and then washed with the culture medium to remove unattached cells. The sample was added to the macrophages so that the final concentration of the sample solution of ginseng berry-purified fraction was 0.8 μg/ml to 100 μg/ml, and the cells were cultured for 72 hours. After completion of the culturing, centrifugation was performed at 900 rpm for 5 minutes to collect 150 μl of supernatant of the cell culture medium, and the content of IL-12, an inducible secretory cytokine, in the culture supernatant was measured. The results are illustrated in FIG. 7.

The polysaccharides of Preparation Example 1 and Preparation Example 2 were used as the samples and PSK (Krestin™, from *Coriolus versicolor*), CVT200 (COLD-FX) prepared from *Panax quinquefolius* root, and Biobran (arabinoxylan compound) were used as the positive controls. In FIG. 7, NC denotes a non-treated group and PC denotes a group treated with LPS at 5 μg/ml.

Figure 7:
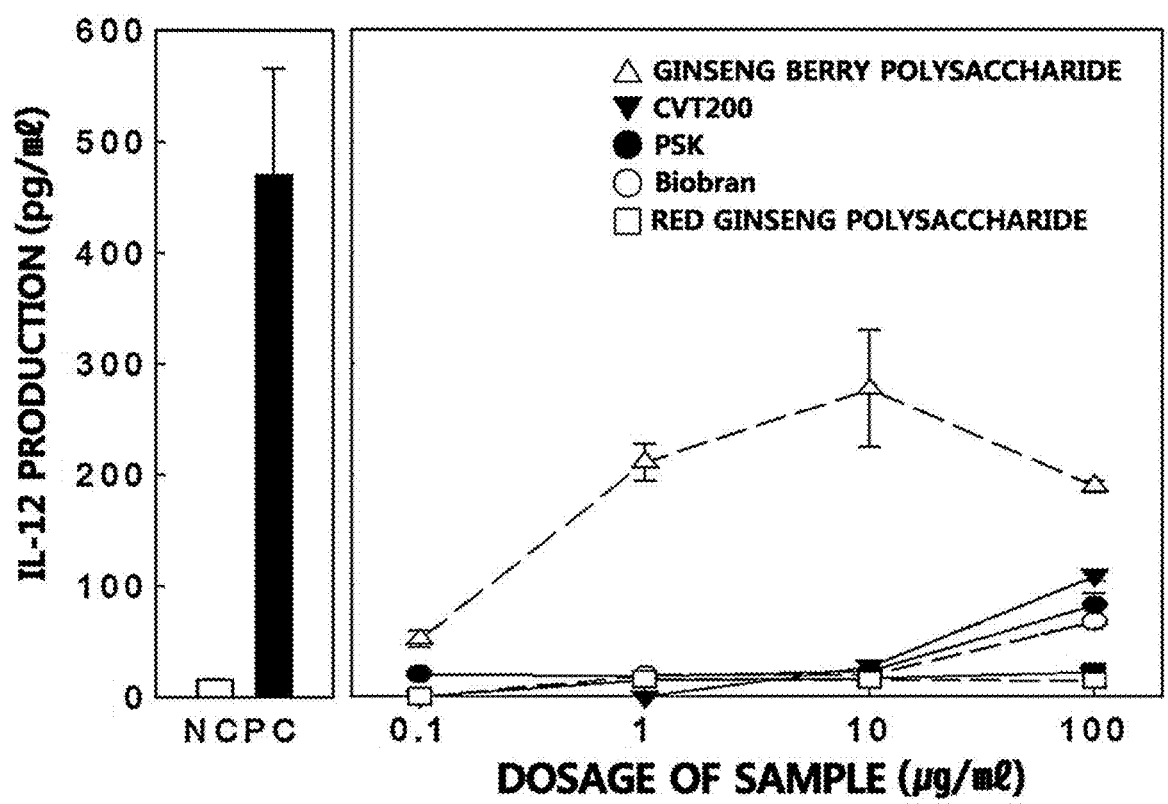
FIG. 7 is a graph which illustrates the IL-12 production ability of a sample in macrophages.

From the results illustrated in FIG. 7, it can be seen that the ginseng berry polysaccharide exhibits remarkably excellent IL-12 production ability as compared with the samples used as the positive control and the red ginseng polysaccharide.

[Test Example 4] Evaluation on TNF-α Production Ability in Macrophage

The TNF-α production ability of ginseng berry polysaccharide in macrophages was measured as follows.

BALB/c mice were intraperitoneally injected with 1 ml of 5% thioglycollate, after 3 days, the mice were sacrificed by cervical dislocation, and peritoneal exudative cells (PEC) were collected by intraperitoneal injection of 10 mL of DMEM medium. The collected PECs were dispensed into a 96-well culture plate so as to have a concentration of $2.0 \times 10^5$ cells/well, cultured for 2 hours to attach macrophages to the plate, and then washed with the culture medium to remove unattached cells. The sample was added to the macrophages so that the final concentration of the sample solution of ginseng berry-purified fraction was 0.8 μg/ml to 100 μg/ml, and the cells were cultured for 72 hours. After completion of the culturing, centrifugation was performed at 900 rpm for 5 minutes to collect 150 μl of supernatant of the cell culture medium, and the content of TNF-α, an inducible secretory cytokine, in the culture supernatant was measured. The results are illustrated in FIG. 8.

The polysaccharides of Preparation Example 1 and Preparation Example 2 were used as the samples and PSK (Krestin™, from *Coriolus versicolor*), CVT200 (COLD-FX) prepared from *Panax quinquefolius* root, and Biobran (arabinoxylan compound) were used as the positive controls. In FIG. 8, NC denotes a non-treated group and PC denotes a group treated with LPS at 5 μg/ml.

Figure 8:
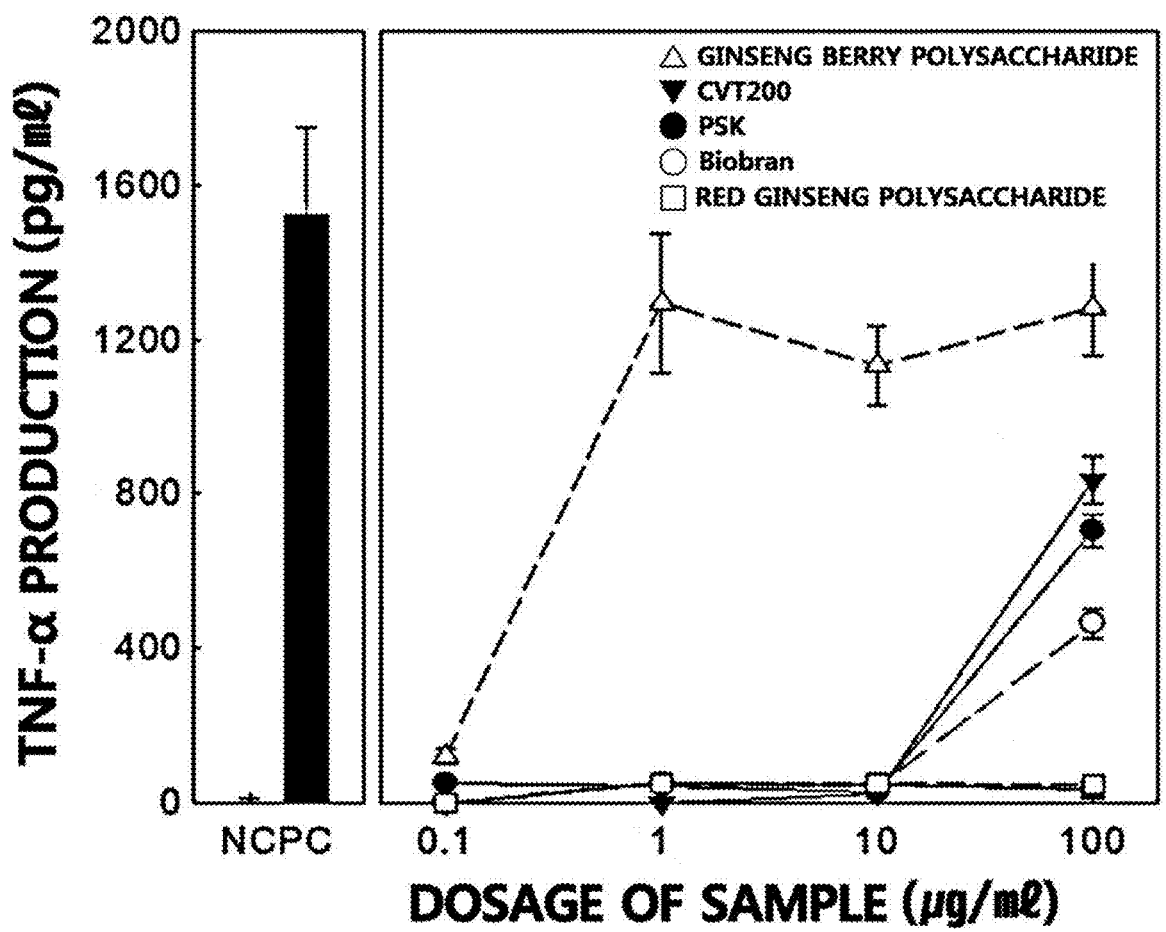
FIG. 8 is a graph which illustrates the TNF-$\alpha$ production ability of a sample in macrophages.

From the results illustrated in FIG. 8, it can be seen that the ginseng berry polysaccharide exhibits remarkably excellent TNF-α production ability as compared with the samples used as the positive control and the red ginseng polysaccharide.

[Formulation Example 1] Tablet

Tablets were prepared by mixing 100 mg of the polysaccharide of Preparation Example 1, 400 mg of lactose, 400 mg of corn starch, and 2 mg of magnesium stearate and then tableting the mixture according to a conventional method for preparing tablets.

[Formulation Example 2] Capsule

Capsules were prepared by mixing 100 mg of the polysaccharide of Preparation Example 1, 400 mg of lactose, 400 mg of corn starch, and 2 mg of magnesium stearate and filling the mixture in gelatin capsules according to a conventional method for preparing capsules.

[Formulation Example 3] Granule

Mixed were 50 mg of the polysaccharide of Preparation Example 1, 250 mg of anhydrous crystalline glucose, and 550 mg of starch, the mixture was formed into granules by using a fluidized bed granulator, and the granules were then filled in a bag.

[Formulation Example 4] Drinkable Preparation

Mixed were 50 mg of the polysaccharide of Preparation Example 1 of the present invention, 10 g of glucose, 0.6 g of citric acid, and 25 g of liquid oligosaccharide, 300 ml of purified water was then added to the mixture, and the resultant mixture was filled in bottles by 200 ml for each. The mixture filled in bottles was sterilized at 130° C. for 4 to 5 seconds, thereby preparing a drinkable preparation.

[Formulation Example 5] Injection

An injection was prepared according to the composition presented in the following table by a conventional method.

TABLE 1

| Ingredients mixed | Content |
|---|---|
| Polysaccharide of Preparation Example 1 | 10-50 mg |
| Sterilized water for injection | Proper amount |
| pH adjusting agent | Proper amount |

The invention claimed is:

1. A method for enhancing immunity of a subject, comprising administering an effective amount of a ginseng (*Panax ginseng* C.A. Meyer) berry polysaccharide to a subject in need thereof, and
   wherein the ginseng berry polysaccharide is extracted from a water soluble component in an ethanol insoluble fraction of a ginseng berry, and wherein the ginseng berry polysaccharide comprises galacturonic acid and glucuronic acid, and
   wherein the galacturonic acid and glucuronic acid are comprised at from 5 wt % to 25 wt % with respect to a total weight of the ginseng berry polysaccharide.

2. The method according to claim 1, wherein the ginseng berry polysaccharide further comprises arabinose and galactose.

3. The method according to claim 1, wherein the ginseng berry polysaccharide has a reactivity of 40% or more with respect to 100% of a reactivity of standard arabino-$\beta$-3,6-galactan when being treated with $\beta$-glucosyl Yariv reagent.

4. The method according to claim 1, wherein the ginseng berry polysaccharide increases expression of interleukin-6 (IL-6).

5. The method according to claim 1, wherein the ginseng berry polysaccharide increases expression of interleukin-12 (IL-12).

6. The method according to claim 1, wherein the ginseng berry polysaccharide increases expression of tumor necrosis factor-$\alpha$(TNF-$\alpha$).

\* \* \* \* \*